US007973131B2

(12) United States Patent
Shigemori et al.

(10) Patent No.: US 7,973,131 B2
(45) Date of Patent: Jul. 5, 2011

(54) EXTREME THERMOPHILE SINGLE-STRANDED DNA BINDING MUTANT PROTEIN, AND NUCLEIC ACID ISOTHERMAL AMPLIFICATION METHOD OF USE THEREOF

(75) Inventors: Yasushi Shigemori, Kisarazu (JP); Takehiko Shibata, Wako (JP); Tsutomu Mikawa, Wako (JP)

(73) Assignees: Aisin Seiki Kabushiki Kaisha, Kariya-shi (JP); Riken, Wako-shi (JP)

(*) Notice: Subject to any disclaimer, the term of this patent is extended or adjusted under 35 U.S.C. 154(b) by 882 days.

(21) Appl. No.: 11/495,640

(22) Filed: Jul. 31, 2006

(65) Prior Publication Data

US 2007/0092896 A1 Apr. 26, 2007

(30) Foreign Application Priority Data

Jul. 29, 2005 (JP) .................... 2005-220580

(51) Int. Cl.
*C07K 1/00* (2006.01)
*C07K 14/00* (2006.01)
(52) U.S. Cl. .................... 530/350; 435/194; 435/91.1
(58) Field of Classification Search .................... None
See application file for complete search history.

(56) References Cited

U.S. PATENT DOCUMENTS

| 6,235,502 B1 | 5/2001 | Weissman et al. |
| 6,617,137 B2 | 9/2003 | Dean et al. |
| 2005/0277146 A1 | 12/2005 | Shigemori et al. |

FOREIGN PATENT DOCUMENTS

| EP | 0 869 187 A2 | 10/1998 |
| JP | 10-234389 | 9/1998 |
| JP | 2002-525078 | 8/2002 |
| WO | WO 00/15849 | 3/2000 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Randall K. Saiki, et al., "Enzymatic Amplification of β-Golbin Genomic Sequences and Restriction Site Analysis for Diagnosis of Sickle Cell Anemia", Science, vol. 230, Dec. 20, 1985, pp. 1350-1354.
G. Terrance Walker, et al., "Isothermal in vitro amplification of DNA by a restriction enzyme / DNA polymerase system", Proc. Natl. Acad. Sci. USA, vol. 89, Jan. 1992, pp. 392-396.
Product Catalog by Amersham Bioscience: GenomiPhi DNA Amplification Kit, <URL:http://www.jp.amershambiosciences.com/catalog/web_catalog.asp?frame5_Value=912&goods_name=GenomiPhi+DNA+Amplification+Kit> (with English Translation).

Frank B. Dean, et al., "Rapid Amplification of Plasmid and Phage DNA Using Phi29 DNA Polymerase and Multiply-Primed Rolling Circle Amplification", Genome Research, 2001, pp. 1095-1099.
Paul M. Lizardi, et al., "Mutation Detection and single-molecule counting using isothermal rolling-circle amplification" nature genetics, vol. 19, Jul. 1998, pp. 225-232.
Slawomir Dabrowski, et al., "Identification and characterization of single-stranded-DNA-binding proteins from *Thermus thermophilus* and *Thermus aquaticus*—new arrangement of binding domains", XP-002411103, Microbiology, vol. 148, No. 10, Oct. 2002, pp. 3307-3315.
Celia Perales, et al., "Enhancement of DNA, cDNA synthesis and fidelity at high temperatures by a dimeric single-stranded DNA-binding protein", Nucleic Acids Research, XP-002411102, vol. 31, No. 22, Nov. 15, 2003, pp. 6473-6480.
Jin Inoue, et al., "Improvements of rolling circle amplification (RCA) efficiency and accuracy using *Thermus thermophilus* SSB mutant protein" Nucleic Acids Research, XP-002411101, vol. 34, No. 9, 2006, pp. 1-9.
Slawomir Dabrowski, et al., "Cloning and Expression in *Escherichia coil* of the Recombinant His-Tagged DNA Polymerases from *Pyrococcus furiosus* and *Pyrococcus woesei*" Protein Expression and Purification, XP-000917996, vol. 14, vol. 1, 1998, pp. 131-138.
Józef Kur, et al., "Single-stranded DNA-binding proteins (SSBs)—sources and applications in molecular biology", Acta Biochimica Polonica, XP-002411104, vol. 52, No. 3, 2005, pp. 569-574.
U.S. Appl. No. 11/780,284, filed Jul. 19, 2007, Shigemori, et al.
J. Chase et al, "Characterization of the *Escherichia coli* SSB-113 Mutant Single-stranded DNA-binding Protein", The Journal of Biological Chemistry, Jan. 25, 1984, vol. 259, No. 2, pp. 805-814.
D. Richard et al, "Physical and functional interaction of the archaeal single-stranded DNA-binding protein SSB with RNA polymerase", Nucleic Acids Research, Feb. 10, 2004, vol. 32, No. 3, pp. 1065-1074.
W. Sun et al, "Interaction of *Escherichia coli* Primase with a Phage G4ori$_c$-*E. coli* SSB Complex", Journal of Bacteriology, Dec. 1996, vol. 178, No. 23, pp. 6701-6705.
G. Fradkin et al, "The Role of In Vivo Interaction of Single-Strand DNA Binding Protein with DNA Plymerase II", Mol. Biol. (Mosk.), Jan.-Feb. 1988, 22(1), pp. 111-116.
J. Aliotta et al, "Thermostable *Bst* DNA polymerase I lacks a 3' → 5' proofreading exonuclease activity", Genetic Analysis: Biomolecular Engineering, 1996, vol. 12, pp. 185-195.
G. Walker et al, "Detection of *Mycobacterium tuberculosis* DNA with thermophilic strand displacement amplification and fluorescence polarization", Clinical Chemistry, 1996, vol. 42, No. 10, pp. 1604-1608.

(Continued)

Primary Examiner — Richard G Hutson
(74) Attorney, Agent, or Firm — Oblon, Spivak, McClelland, Maier & Neustadt, L.L.P.

(57) ABSTRACT

The invention establishes a technology that allows non-specific amplification to be inhibited during nucleic acid amplification in an isothermal amplification reaction, such that the amplification efficiency is increased. The invention is a extreme thermophile single-stranded DNA binding mutant protein, having an amino acid sequence that expresses a function that can contribute to increasing an amplification efficiency of a template nucleic acid in an isothermal amplification reaction system that uses a strand displacement polymerase, and having in its amino acid sequence a mutation site where a mutation involving at least one of deletion, substitution, addition, and insertion of one or more amino acids in amino acid sequence of extreme thermophile single-stranded DNA binding protein has occurred, and a method of use thereof.

4 Claims, 5 Drawing Sheets

OTHER PUBLICATIONS

K. Matsumoto et al, Primary structure of bacteriophage M2 DNA polymerase: conserved segments within protein-priming DNA polymerases and DNA polymerase I of *Escherichia coli*, Gene, 84 (1989)pp. 247-255.

G. Jung et al, "Bacteriophage PRD1 DNA polymerase: Evolution of DNA polymerases", *Proc. Natl. Acad. Sci. USA*, Dec. 1987, vol. 84, pp. 8287-8291.

H. Kong et al, "Characterization of a DNA Polymerase from the Hyperthermophile Archaea *Thermococcus litoralis*", *The Journal of biological Chemistry*, Jan. 25, 1993, vol. 268, No. 3, pp. 1965-1975.

H. Jacobsen et al, "The N-Terminal Amino-Acid Sequences of DNA Polymerase I from *Escherichia coil* and the Large and the Small Fragments Obtained by a limited Proteolysis", *Eur. J. Biochem.*, 1974, vol. 45, pp. 623-627.

D. Chatterjee et al, "Cloning and overexpression of the gene encoding bacteriophage T5 DNA polymerase", *Gene*, vol. 97, 1991, pp. 13-19.

W. Zhu et al, "Purification and characterization of PRD1 DNA polymerase", *Biochimica et Brophysica Acta*, 1994, vol. 1219, pp. 267-276.

B. Kaboord et al, "Accessory proteins function as matchmakers in the assembly of the T4 DNA polymerase holoenzyme", *Current Biology*, 1995, vol. 5, No. 2, pp. 149-157.

* cited by examiner

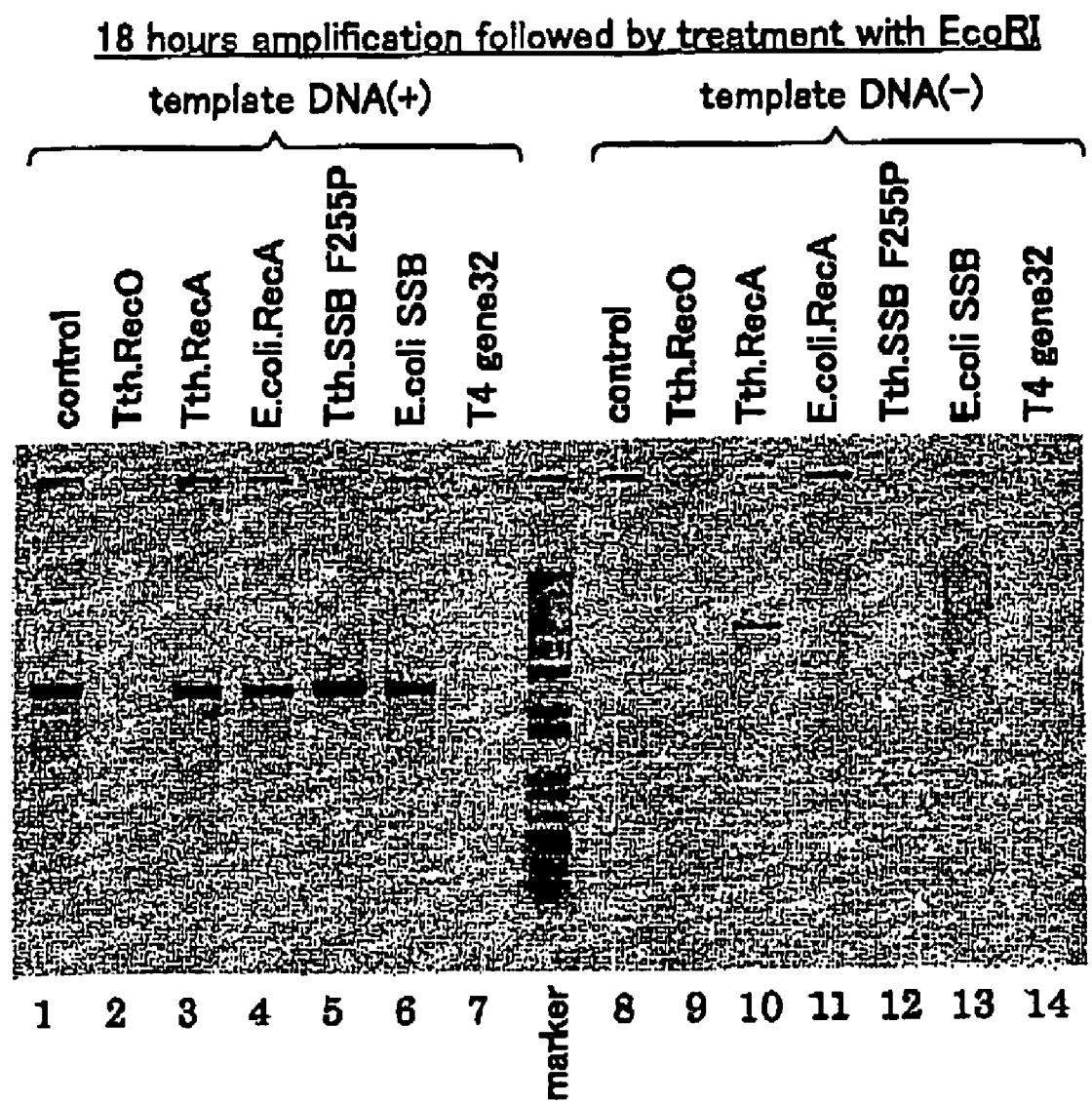

EXTREME THERMOPHILE SINGLE-STRANDED DNA BINDING MUTANT PROTEIN, AND NUCLEIC ACID ISOTHERMAL AMPLIFICATION METHOD OF USE THEREOF

BACKGROUND OF WE INVENTION

1. Field of the Invention

The present invention relates to extreme thermophile single-stranded DNA binding mutant proteins, and methods of use thereof. More specifically, the invention relates to extreme thermophile single-stranded DNA binding mutant proteins that can improve the amplification efficiency of a template nucleic acid in an isothermal amplification system that uses a strand displacement polymerase and methods of use thereof.

2. Description of the Related Art

Various methods for exponentially amplifying nucleic acids have been developed previously, and the methods that amplify nucleic acids particularly efficiently can generally be separated into those that use a thermal cycle in which the reaction temperature fluctuates and those in which the reaction temperature remains constant.

Polymerase chain reaction, that is, PCR (see Non-Patent Document 1, for example), is known as one method that uses a thermal cycle. In PCR, two primers that have a base sequence complementary to a target nucleic acid template are mixed with the template nucleic acid. Next, normally a single cycle involving denaturation of the template nucleic acid, annealing the primers to the template nucleic acid, and extension of the primers by DNA polymerase (DNA replication) is performed for twenty to thirty cycles in order to synthesize a strand complementary to the template nucleic acid between the two primers that have been annealed to the template nucleic acid. In this method, the synthesized strand can serve as a new template nucleic acid, and thus the template nucleic acid can be amplified exponentially through replication in other cycles using the same primer set. To withstand the elevated temperatures that are required to denature the template nucleic acid in each cycle, it is necessary to use a heat-stable DNA polymerase. Further, in DNA amplification by PCR, the amplification reaction does not proceed in a continuous manner and thus the nucleic acid sample, that is, the template nucleic acid, must be supplied over a series of a plurality of cycles as amplification is carried out.

By contrast, strand displacement amplification (SDA) (for example, see Non-Patent Document 2) and rolling circle amplification (RCA) (for example, see Non-Patent Documents 3, 4, and 5) are known as methods in which the template nucleic acid amplification reactions are performed isothermally. In SDA, a restriction enzyme nicks a template nucleic acid and the action of a DNA polymerase (strand displacement polymerase), which one by one displaces these DNA fragments having nicks, is used to amplify the DNA. RCA, on the other hand, involves displacement by a strand displacement polymerase of the strand before the tip of an elongation strand that has been synthesized, with using, as its origin, a primer annealed to a template nucleic acid in order to produce a hybrid. These methods therefore do not require a thermal cycle because amplification of target DNA sequences is carried out isothermally in a continuous manner.

Such strand displacement allows template nucleic acids to be linearly or exponentially amplified in a continuous manner under isothermal conditions. Consequently, some advantages to RCA, for example, include that it can more efficiently increase the amount of amplification product that is produced because the procedure of template nucleic acid amplification is simpler than methods that use a thermal cycle, that there are no limitations regarding the length of template nucleic acids that can be amplified effectively, and that equipment for performing the thermal cycle is not necessary.

Here, in the template nucleic acid amplification reaction, single-stranded DNA binding protein (hereinafter may also be abbreviated as "SSB protein") is known to be related to the efficiency of the template nucleic acid amplification reaction, for example.

SSB protein has high affinity for single-stranded DNA (ssDNA) in a manner that is not sequence specific. Normally, SSB protein is necessary or DNA replication and recombination and for repair of the organism genome. SSB protein specifically stimulates homologous DNA polymerase, increases the fidelity of DNA synthesis, improves the ability of DNA polymerase to advance forward by destabilizing the helix and promotes DNA polymerase binding, and organizes and stabilizes the replication origin. That is, SSB protein is known to act as a replication assisting protein (for example, see Patent Documents 1 and 2).

Numerous examples of SSB proteins have been isolated from a wide array of sources ranging from bacteriophages to eukaryotes. For example, Patent Document 1 discloses the replication protein A-1 (rpa-1) from beer yeast (*Saccharomyces cerevisiae*), a mitochondrial replication protein (rim-1), the bacteriophage T7 gene 2.5 protein (gp 2.5), the bacteriophage phi29 protein p5 (p5), the T4 gene 32 protein (gp32), and the *Escherichia coli* SSB protein. It is also known that SSB protein has been isolated from extreme thermophiles as well (for example, see Non-Patent Documents 6 and 7).

Patent Document 1 describes the addition of SSB protein to an isothermal amplification reaction system in order to improve the efficiency of template nucleic acid amplification. In Patent Document 2, *E. coli* SSB protein is used as an effective strand displacement factor for the strand displacement replication of a template nucleic acid. That is, it discloses that, in the presence of the strand displacement factor, a strand displacement polymerase that can carry out strand displacement replication (such as the bacteriophage phi29 DNA polymerase) is used to amplify template nucleic acid through RCA.

These template nucleic acid amplification methods that use strand displacement polymerases are dependent on the strand displacement ability of that strand displacement polymerase, which denatures the template nucleic acid. Since strand displacement can be promoted by replication assisting proteins and strand displacement factors, it was thought that the presence of replication assisting proteins or strand displacement factors would allow DNA fragments that are specific to the template nucleic acid to be amplified efficiently.

Patent Document 1: JP H10-284889A (see paragraphs 0007 and 0014, for example)
Patent Document 2: JP 2002-525078A (see paragraphs 0059 to 0062, for example)
Non-Patent Document 1: Saiki et al., Science 230:1350-1354, 1985
Non-Patent Document 2: Walker et al., Proc. Natl. Acad. Sci. USA 89: 392-896, 1992
Non-Patent Document 3: Amersham Biosciences, "Product Catalog: GenomiPhi DNA Amplification Kit," online, searched on the Internet on Apr. 28, 2005, <URL: http://www.jp.amershambiosciences.com/catalog/web_catalog.asp?frame5_Value=912&goods_name=GenomiPhi+DNA+Amplification+Kit>
Non-Patent Document 4: Dean et al., Genome Res. 11(6), 1095-1099, June 2001

Non-Patent Document 5: Lizardi et al., Nature Genetics 19(3), 225-282, July 1998

Non-Patent Document 6: Dabroski et al., Microbiology, 148 (Pt10), 3307-3315, October 2002

Non-Patent Document 7: Perales et al., Nucleic Acids Research, 31(22), 6473-6480, November 2003

However, in isothermal amplification systems that use a strand displacement polymerase there is the problem that, although DNA fragments that are specific to the template nucleic acid amplified efficiently, DNA fragments that are non-specific to the template nucleic acid also are easily amplified as well. The methods disclosed in Patent Documents 1 and 2 involve adding SSB protein from E. coli or yeast to carry out the isothermal amplification reaction, and in these methods as well there was the problem that it was not possible to inhibit the amplification of non-specific DNA fragments.

A possible reason or this is that the temperature during isothermal amplification normally is about 30 to 60° C. and thus primer dimers readily form, and these primer dimers that have formed increase the likelihood that DNA fragments that are non-specific for the template nucleic acid will be amplified. In other words, primer dimers are formed even when a template nucleic acid is not present and lead to the amplification of non-specific nucleic acids. DNA fragments that are non-specific for a template nucleic acid lower the amplification precision and become background noise that impedes later experiments. Since primers with random sequences are used in the amplification, it was believed to be difficult to control non-specific amplification.

For these reasons, isothermal amplification methods for template nucleic acids have the potential to become widespread due to the fact that they do not require a thermal cycle like PCR, for example, but at the present time they have found only limited application due to problems with the amplification precision resulting from the non-specific amplification discussed above.

SUMMARY OF THE INVENTION

It is therefore an object of the invention to establish a technology that can keep non-specific amplification in check during template nucleic acid amplification through isothermal amplification reaction in order to increase the amplification precision.

After performing keen investigations, the inventors constructed a extreme thermophile single-stranded DNA binding mutant protein having an amino acid sequence that includes a mutation site where a mutation has occurred to a particular amino acid in an amino acid sequence included in the extreme thermophile single-stranded DNA binding protein. When the extreme thermophile single-stranded DNA binding mutant protein was added to an isothermal amplification system that uses a strand displacement polymerase, it was found that an amplification product specific for the template nucleic acid was obtained, that non-specific amplification did not occur, and that the amplification product could be obtained with high precision. The present invention was arrived at based on these findings.

To achieve the foregoing goals, the invention provides a extreme thermophile single-stranded DNA binding mutant protein, having an amino acid sequence that expresses a function that can contribute to increasing an amplification efficiency of a template nucleic acid in an isothermal amplification reaction system that uses a strand displacement polymerase, and having in its amino acid sequence a mutation site where a mutation involving at least one of deletion, substitution, addition, and insertion of one or more amino acids in amino acid sequence of extreme thermophile single-stranded DNA binding protein has occurred, and preferably, the extreme thermophile single-stranded DNA binding mutant proteins a single-stranded DNA binding protein from Thermus thermophilus or Thermus aquaticus.

It is also preferable that the mutation results in a change in the interaction of the extreme single-stranded DNA binding protein with strand displacement polymerase and that the mutation results in a change in the DNA binding ability of the extreme thermophile single-stranded DNA binding protein.

It is further preferable that the mutation occurs in the amino acid sequence of the extreme thermophile single-stranded DNA binding protein in such a manner that the amino acid sequence has at least three contiguous proline residues.

Specifically, it is preferable that the mutation is a mutation in which phenylalanine 255 of the amino acid sequence Sequence Number 1 showing the Thermus thermophilus single-stranded DNA binding protein has been substituted by another amino acid, or that the mutation is a mutation in which phenylalanine 256 of the amino acid sequence Sequence Number 4 showing the Thermus aquaticus single-stranded DNA binding protein has been substituted by another ado acid. In particular, the other amino acid is proline.

Also, to achieve the foregoing objects, the present invention provides a nucleic acid isothermal amplification method using a strand displacement polymerase, in which an amplification reaction is performed with addition of the extreme thermophile single-stranded DNA binding mutant protein of the invention, and preferably, the strand displacement polymerase is phi29 DNA polymerase.

By adding the extreme thermophile single-stranded DNA binding mutant protein of the invention to a DNA isothermal amplification system that uses a strand displacement polymerase, it becomes possible to efficiently amplify specific DNA fragments, which was not possible to achieve with single-stranded DNA binding proteins from an extreme thermophile that do not have the mutation site or with other recombination-related proteins. That is, non-specific amplification can be inhibited, it is possible to amplify DNA fragments without being affected by background noise, and it is possible to contribute to increasing the amplification efficiency.

Consequently, an amplification method that utilizes the extreme thermophile single-stranded DNA binding mutant protein of the invention can be broadly utilized in general molecular biology methods. For example, this method is useful, for the purpose of genotyping, in a method for preparing large quantities of DNA from a small sample amount that has been extracted from a minute quantity of microorganism collected from the environment for the purpose of gene analysis, or as a method of preparing DNA for DNA sequencing. This method also has significant value in terms of preparing very generalized DNA that can be adopted in various applications, such as preparing DNA for chip immobilizing from a small sample amount that has been extracted from an animal or plant cell.

The extreme thermophile single-stranded DNA binding mutant protein of the invention also can be adopted in a system for cloning target cDNA clones from a DNA library. By doing this, it is possible to specifically and efficiently concentrate or isolate target cDNA clones from a DNA library. Specific and efficient cDNA cloning has the potential to significantly contribute to the analysis of gene expression, generation, differentiation, and to the production of useful compounds.

The extreme thermophile single-stranded DNA binding mutant protein of the invention can be adopted in a reverse transcription reaction system from RNA to DNA. Thus, a desired target RNA can be specifically and efficiently transformed into cDNA. Because conversion from RNA to cDNA is a technique that is indispensable to genetic engineering, this invention is valuable for detecting and quantifying gene expression, RNA structure analysis, and cDNA cloning, among others.

Hereinafter, the extreme thermophile single-stranded DNA binding mutant protein of the invention also may be abbreviated as "extreme thermophile SSB mutant protein." The extreme thermophile single-stranded DNA binding protein may also be abbreviated as "extreme thermophile SSB protein."

BRIEF DESCRIPTION OF THE DRAWINGS

FIG. 8 is an electrophoresis pattern showing the results of Working Example 7, in which the samples of Working Example 6 were subjected to restriction by restriction enzymes and then subjected to electrophoresis.

DETAILED DESCRIPTION OF THE PREFERRED EMBODIMENTS

Figure 1:
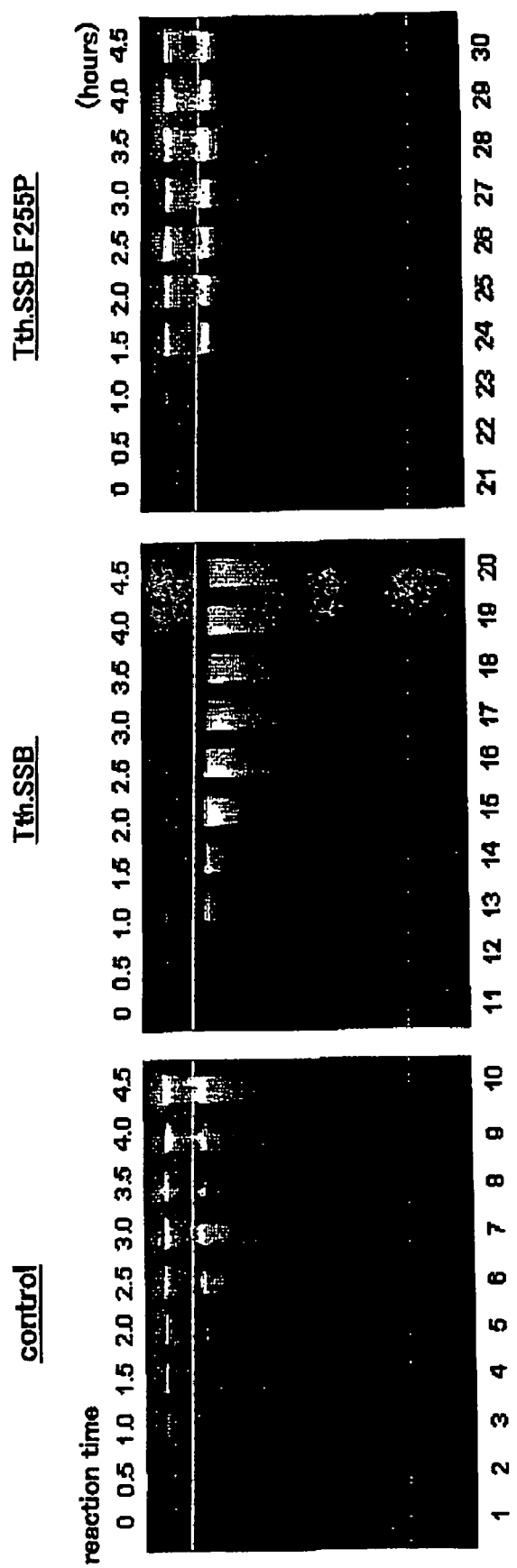
FIG. 1 is an electrophoresis pattern showing the results of Working Example 1, in which the effects that the extreme thermophile SSB protein and the extreme thermophile SSB mutant protein have on the isothermal amplification reaction system in the presence of a template nucleic acid are compared and evaluated.

The invention is described in detail below.

The extreme thermophile single-stranded DNA binding mutant protein of the invention includes all mutant forms of an single-stranded DNA binding protein that express a function that can contribute to improving the template nucleic acid amplification efficiency in an isothermal amplification reaction system that uses a strand displacement polymerase. In other words, compared to the extreme thermophile single-stranded DNA binding protein, the single-stranded DNA binding mutant protein of the invention has improved specificity for the template nucleic acid in an isothermal amplification reaction system that uses a strand displacement polymerase. Further, the extreme thermophile single-stranded DNA binding mutant protein has a mutation site in which specific amino acids in an amino acid sequence of an extreme thermophile single-stranded DNA binding protein have been mutated. Mutation is here used to mean a mutation involving at least one of a deletion, substitution, insertion, or addition to one or more amino acids in the amino acid sequence of the protein serving as the basis for mutation. Here, the "mutation involving at least one of a deletion, substitution, insertion, or addition to one or more amino acids" means mutation involving deletion, substitution, insertion or addition of such a number of amino acids that can be deleted from, substituted for, inserted or added to the gene encoding the protein serving as the basis of mutation, by application of a known technique such as DNA recombination, point mutation, etc or combination thereof.

Such mutations can be induced artificially or can occur unintentionally in nature. The extreme thermophile single-stranded DNA binding mutant protein of the invention includes both types of mutations.

Hereinafter, the extreme thermophile single-stranded DNA binding mutant protein of the invention also may be abbreviated as "extreme thermophile SSB mutant protein." The extreme thermophile single-stranded DNA binding protein may also be abbreviated as "extreme thermophile SSB protein." Here, in cases where this has been abbreviated to simply "extreme thermophile single-stranded DNA binding protein" or "extreme thermophile SSB protein," does not include a mutation site such as the one described above in its amino acid sequence.

An extreme thermophile SSB protein from *Thermus thermophilus* or *Thermus aquaticus* is a preferable example of the extreme thermophile SSB protein that serves as the basis for the mutant form. This is not a limitation, however. It should be noted that "extreme thermophile SSB protein" means the amino acid sequence of the SSB protein found in an extreme thermophile that has been isolated from nature, and the base sequence encoding that SSB protein, does not have mutation sites in which intentional or unintentional mutations have occurred.

The extreme thermophile SSB mutant protein of the invention can be obtained by a method known to the public. For example, it is possible to cause a mutation in the gene encoding the extreme thermophile SSB protein serving as the basis for the mutant form, use the mutant gene that is yielded to transform a host cell, and then culture the transformant and obtain the extreme thermophile SSB protein from that culture.

The gene for the extreme thermophile SSB protein can be obtained using a gene cloning technique that is known to the public. It is also possible to obtain the extreme thermophile SSB protein by synthesize it using a DNA synthesis method such as the standard phosphoramidite method, based on gene information that can be obtained by searching a public database such as GenBank. Here, as the sequence information of a preferable extreme thermophile SSB protein that can serve as the basis for the mutant form of the invention, the amino acid sequence of *Thermus thermophilus* SSB is shown in Sequence Number 1 and the base sequence of the gene encoding that SSB protein is shown in Sequence Number 2 (GenBank: AJ564626). The amino acid sequence of an SSB protein of *Thermus aquaticus* is shown in Sequence Number 4, and the base sequence of the gene encoding that SSB protein is shown in Sequence Number 6 (GenBank: AF276705).

There are no particular restrictions regarding the method for causing a mutation in the gene encoding the extreme thermophile SSB protein, and mutation inducing techniques for producing mutant proteins that are known to the public and are familiar to those skilled in the art can be adopted. For example, it is possible to use a publicly known mutation inducing technique such as site-directed mutagenesis, PCR mutagenesis that employs PCR or the like to induce point mutations, or transposon insertional mutagenesis, etc. For example, public documents (such as Chase, J W et al., The Journal of Biological Chemistry, 259(2), 805-814, Jan. 25, 1984) related to inducing, mutations to *E. coli* SSB proteins can be referenced. It is also possible to use a commercially available mutation induction kit (such as QuikChange™ Site-directed Mutagenesis Kit (made by Stratagene)). Alternatively, once the target amino acid sequence of the extreme thermophile SSB mutant protein has been chosen, it is possible to determine the appropriate base sequence that encodes that amino acid sequence, and then employ a DNA synthesis method such as the standard phosphoramidite method to synthesize DNA that code for the extreme thermophile SSB mutant protein of the invention.

It is possible to use a commonly known host-expression vector system, in which the host is known to the public, such as *E. coli*, to transform a host cell using the mutant gene that has been obtained. For example, the extreme thermophile SSB mutant protein can be linked to a DNA vector in which it can be stably amplified, and then is transferred into *E. coli* that can efficiently express the extreme thermophile SSB mutant protein. This is then seeded on a medium that includes a carbon source, a nitrogen source, and other essential nutrients and then cultured according to a standard method express the extreme thermophile SSB mutant protein.

The collection and purification of extreme thermophile SSB mutant protein from the culture of the transformant thus obtained are carried out according to standard methods. For example, by disrupting and then heat-treating the host *E. coli*, the *E. coli* derived proteins other than the extreme thermophile SSB mutant protein are heat denatured and aggregate under the heat, and thus can be separated away by centrifugation, for example. The extreme thermophile SSB mutant protein, which is not heat denatured by this, is separated from the *E. coli* proteins as the soluble fraction and can be purified using affinity chromatography, for example.

At this time, the extreme thermophile SSB protein structure is stable at room temperature because the protein is from an extreme thermophile, and it also has a high degree of stability with respect to organic solvents. Thus, the above purification process can be carried out at room temperature.

It should be noted that as long as the expression vector includes e.g. a promoter sequence and a sequence such as a multicloning site having at least one restriction enzyme site to which a gene encoding the extreme thermophile SSB mutant protein of the invention can be inserted, and can express the inventive extreme thermophile SSB protein in the host cell, then any expression vector can be used. As an example of a favorable promoter, it is preferable that the T7 lac promoter is adopted.

It is also possible for the expression vector to include other base sequences that are known to the public. There are no limitations regarding the other base sequences known to the public. Possible examples thereof include a stable leader sequence that gives stability to the expression product, and a signal sequence that facilitates secretion of the expression product. The vector can include also a marking sequence that can give phenotype selectivity to a transformed host. Some non-limiting examples of such marking sequence are a neomycin-resistant gene, a kanamycin-resistant gene, a chloramphenicol-resistant gene, an ampicillin-resistant gene, and a hygromycin-resistant gene.

It is possible to use a commercially available *E. coli* expression vector (such as the pET protein expression system, made by Novagen) as this expression vector, and it is also possible to fabricate and use an expression vector that suitably incorporates the desired sequence.

The host cell is not limited to *E. coli* and it is also possible to use *Bacillus* bacteria or *Pseudomonas* bacteria, for example. There is no limitation to prokaryotes, and it is also possible to use eukaryotic cells as well. For example, yeast such as *Saccharomyces cerevisiae*, insect cells such as Sf9 cells, or animal cells such as CHO cells or COS-7 cells, can be used favorably.

Whether or not the purified SSB protein is an extreme thermophile SSB mutant protein that has a mutation site in which the desired mutation has occurred can be confirmed using an amino acid analysis method that is known to the public. For example, an automatic amino acid determination method based on Edman sequencing can be used. This can also be confirmed by using the purified SSB protein in an isothermal amplification reaction that uses a strand displacement polymerase and comparing it with the extreme thermophile SSB protein without the mutation site to confirm whether or not specificity for the template nucleic acid has increased. This confirmation can for example be performed using the method illustrated in the working examples of the invention.

Here, the "function that can contribute to improving the template nucleic acid amplification efficiency" means that, in an isothermal amplification reaction that uses a strand displacement polymerase, hardly any non-specific amplification that is unrelated to the template nucleic acid is observed, and it is possible to amplify the template nucleic acid with high yield. Preferably this also means a function that can increase the template nucleic acid amplification efficiency by a factor of 5 to 10. For example, this means that the function is substantially identical to the function of the protein with the amino acid sequence shown in Sequence Number 8 or 6, which can contribute to improving the template nucleic acid amplification efficiency in an isothermal amplification reaction system that uses a strand displacement polymerase.

As the extreme thermophile SSB mutant protein of the invention, an extreme thermophile SSB mutant protein that has a mutation in its amino acid sequence that causes a change in how it interacts with the strand displacement polymerase can be preferably adopted. An extreme thermophile SSB mutant protein having a mutation that results in a change in the DNA binding ability of the extreme thermophile single-stranded DNA binding protein also may be preferably adopted.

That is, there is a possibility that the extreme thermophile SSB mutant protein of the invention affects the interaction with the strand displacement DNA polymerase in some manner. Here, the interaction with the strand displacement polymerase refers to the interaction between the extreme thermophile SSB protein and the strand displacement polymerase, the interaction between the extreme thermophile SSB protein and the DNA, or the interaction between the extreme thermophile SSB protein, the strand displacement polymerase, and the DNA. Here, DNA is single-stranded DNA and is used to mean either one or both of a primer or a single strand portion of the template nucleic acid. Further, the "change in how the extreme thermophile SSB protein interacts with the strand displacement polymerase" means that a change occurs in the action that the extreme thermophile SSB protein originally had on the strand displacement polymerase. It has been reported that SSB proteins from *E. coli* and *Sulfolobus sulfataricus* among others, bind not only single-stranded DNA but also polymerases such as primase, RNA polymerase, and DNA polymerase II (or example, see Richard D J et al., Nucleic Acids Res. Feb. 10, 2004; 32(3): 1065-74, Sun W. et al., J Bacteriol. December 1996; 178(23): 6701-5, Fradkin G E et al., Mol Biol (Mosk). January-February 1988; 22(1): 111-6). Thus, when the SSB protein has been added to an isothermal amplification system that uses a strand displacement polymerase, the SSB protein assists the strand displacement reaction, but on the other hand it can also be anticipated that it will exhibit the undesirable action of lowering polymerase activity and therefore the amplification efficiency also. This expectation is in agreement with the results of the working examples described below, in which the presence of *E. coli* SSB or the extreme thermophile SSB led to a drop in the amplification efficiency. Accordingly, a preferable example of the extreme thermophile SSB mutant protein of the invention is one in which the amino acid sequence has been disrupted in the region that gives the SSB protein its polymerase binding ability. Also, it can be presumed that the "change in how the extreme thermophile SSB protein interacts with the strand displacement polymerase" includes a change in which there is a drop in, or a loss of, the original ability of the extreme thermophile SSB protein to bind the strand displacement polymerase.

Specifically, one illustrative example of the extreme thermophile SSB mutant protein of the invention is one in which the amino acid sequence of the extreme thermophile SSB protein has been mutated such that it has at least three contiguous proline residues. That is, the extreme thermophile SSB mutant protein of the invention preferably includes the sequence Pro-Pro-Pro in its amino acid sequence, and it is also possible for there to be one or more proline residues before or after that sequence.

In this invention, in particular it is preferable that, for example, phenylalanine 255 of Sequence Number 1, which shows the *Thermus thermophilus* SSB protein, or phenylalanine 256 of Sequence Number 4, which shows the *Thermus aquaticus* SSB protein, has been substituted by another amino acid. As this other amino acid, proline is a particularly preferable example. Sequence Number 3 shows the amino acid sequence of the extreme thermophile SSB mutant protein of the invention in which phenylalanine 255 of Sequence Number 1, which shows the *Thermus thermophilus* SSB protein, has been replaced by proline. Sequence Number 6 shows the amino acid sequence of the extreme thermophile SSB mutant protein of the invention in which phenylalanine 256 of Sequence Number 4, which shows the *Thermus aquaticus* SSB protein, has been replaced by proline.

The invention also provides a method for the isothermal amplification of a template nucleic acid that uses a strand displacement polymerase with which isothermal amplification is possible, and uses the extreme thermophile SSB mutant protein of the invention. The amplification method of the invention performs an amplification reaction with addition of the extreme thermophile SSB mutant protein of the invention.

Here, the isothermal amplification method using a strand displacement polymerase is a method for exponentially amplifying a nucleic acid through strand displacement activation of the strand displacement polymerase, under isothermal conditions in which heat denaturation through elevated temperatures is not required. Rolling circle amplification Hereinafter may be abbreviated as "RCA") is a preferable example of such an isothermal amplification method using a strand displacement polymerase. The principle of RCA is as follows. Isothermal amplification of a template nucleic acid by RCA involves a strand displacement polymerase elongating, under isothermal condition, a strand complementary to circular DNA, that is, the template nucleic acid, with using, as the origin, a plurality of random primers that have been annealed to the circular DNA. Then, as the synthesized strand is elongated and this elongation reaches the replication origin of another random primer, it continues elongation of the strand while peeling off the other synthesized strand through strand displacement activation (branching). This exposes sites on the synthesized strand that has been peeled off to which a random primer can be annealed. That is to say, the circular DNA as well as the synthesized strand that has been peeled off serve as template nucleic acids from which new DNA synthesized strands can be formed, and thus the amplification is exponential.

As for the random primer that is used as this time, it is possible to favorably use a random hexamer, for example. Other primers that may be adopted include primers that specifically anneal to a target site on the template nucleic acid at a setting temperature. These primers can be used alone or in combination with other random primers.

The primers are designed by primer design support software or the like based on a target nucleic acid sequence so that a desired region is amplified, and in the case of random primers, the primers are designed so that their sequence is random. Primers designed in this fashion can be chemically synthesized. For example, they can be chemically synthesized by solid phase synthesis using the publicly-known phosphoramidite method and primers of a desired base sequence can be automatically synthesized using a commercially available automatic nucleic acid synthesis device. After synthesis of the primers, if necessary they may be purified by a method that is known to the public, such as HPLC.

Here, "isothermal" in the context of isothermal amplification indicates that the amplification reaction is performed keeping the temperature constant, in contrast to PCR, in which the reaction temperature is changed in each process for DNA denaturation, annealing, and strand elongation. The fixed temperature at which the amplification reaction is performed is preferably below 60° C., more preferably below 45° C., and most preferably below 37° C. This temperature is suitably set based on the strand displacement polymerase that is adopted. For example, if the bacteriophage phi29 DNA polymerase, which is described later, is used, then the ideal temperature range at which to perform the amplification reaction is 25 to 42° C., preferably 30 to 37° C., and most preferably 30 to 34° C. The sample is incubated or about 4 to 24 hours, preferably 6 to 24 hours, and most preferably 15 to 24 hours, in an incubation chamber such as an incubator that has been set to the fixed temperature, so as to carry out the template nucleic acid amplification reaction.

A preferable example of the strand displacement polymerase is the bacteriophage phi29 DNA polymerase (U.S.

Pat. No. 5,198,543 and U.S. Pat. No. 5,001,050, Blanco et al.). However, this is not a limitation. For example, the Bst DNA polymerase large fragment (Exo(−)Bst) (Aliotta et al., Genet. Anal. (Netherlands) 12:185-195 (1996)) and Exo(−) Bca DNA polymerase (Walker and Linn, Clinical Chemistry 42:1604-1608 (1996)), Phage M2 DNA polymerase (Matsumoto et al., Gene 84: 247 (1989)), Phage φ PRD1 DNA polymerase (Jung et al., Proc. Natl. Acad. Sci. USA 84:8287 (1987)), VENT™ DNA polymerase (Kong et al., J. Biol. Chem. 268:1966-1975 (1993), Klenow fragment of DNA Polymerase I (Jacobsen et al., Eur. J. Biochem. 45:623-627 (1974)), T5 DNA polymerase (Chatterjee et al., Gene 97:13-19 (1991)), Sequenase™ (US Biochemicals), PRD1 DNA polymerase (Zhu and Ito, Biochem. Biophys. Acta. 1219: 267-276 (1994)) and T4 DNA polymerase holoenzyme (Kaboord and Benkovic, Curr. Biol. 5:149-157 (1995)).

As the template nucleic acid, circular DNA is a favorable example but this is not a limitation, and it is also possible to use linear DNA. In the case of RCA, circular DNA is favorable from the standpoint of amplification efficiency. The template nucleic acid can be single stranded or double stranded. Various types of DNA molecules also can serve as the template nucleic acid, such as natural DNA including plasmid DNA and eukaryotic and prokaryotic genome DNA, and artificially created DNA molecules such as bacterial artificial chromosome (BAC) DNA, phagemids, and cosmids. Synthetic DNA such as oligonucleotides also can serve as the template nucleic acid.

By adopting the above configuration, it is possible to efficiently amplify DNA fragments that are specific to a template nucleic acid. That is, non specific amplification that is not related to the template nucleic acid can be inhibited, and thus DNA fragment amplification that is not affected by background noise becomes possible.

The extreme thermophile SSB mutant protein of the invention also can be adopted for concentrating or isolating a target cDNA clone from a DNA library. More specifically, the extreme thermophile SSB mutant protein of the invention can be adopted when amplification is conducted using part of the sequence of a target cDNA to be concentrated or isolated as a primer and taking the DNA library as the template. Here, the amplification reaction can be performed utilizing an isothermal amplification reaction system that uses a strand displacement polymerase, as well as others such as an ordinary PCR reaction system. Thus, it is possible to inhibit non-specific amplification that is not related to the target cDNA, and it becomes possible to specifically amplify only the target cDNA. Thus, by adopting the extreme thermophile SSB mutant protein of the invention in a cloning system for cloning a target cDNA from a DNA library, it is possible to specifically and efficiently concentrate and isolate a desired target cDNA clone.

Here, as the DNA library it is possible to use a DNA library that includes, or is expected to be capable of including, target DNA regions for which it is desirable to concentrate or isolate. The DNA library can be either a gene library or a cDNA library, and in particular it is preferably a cDNA library. It should be noted that in this specification, gene library is used conceptually to mean a population of cloned DNA obtained by randomly integrating the entire genome DNA of a specific single species into a vector. On the other hand, cDNA library is used conceptually to mean a population of cDNA fragments created by synthesizing cDNA by reverse transcription from the mRNA of a specific tissue, cell, or organism and integrating this into a vector.

Primers normally are designed to be complementary to a specific sequence of a target nucleic acid. In particular, primers having a base sequence complementary to both ends of a target sequence to be amplified are preferable, and in this invention, the sequence of a portion of a target cDNA for which there is an interest to concentrate or isolate can be favorably used as a primer. It should be noted that primer design is public knowledge, and the primer is designed based on the base sequence of the target cDNA, and for example it is possible to use primer design support software. A primer designed in this manner can be chemically synthesized. For example, primers can be chemically synthesized by solid phase synthesis using the publicly-known phosphoramidite method, and primers of a desired base sequence can be automatically: synthesized using a commercially available automatic nucleic acid synthesis device. After synthesis of the primers, if necessary they may be purified by a method known to the public such as HPLC.

The extreme thermophile SSB mutant protein of the invention can be adopted in a reverse transcription reaction from RNA to DNA. More specifically, the extreme thermophile SSB mutant protein of the invention can be adopted when cDNA is to be synthesized from RNA by reverse transcription in the presence of a reverse transcription enzyme using a random primer, an oligo dT primer, or a target gene specific primer. It also can be adopted when the amplification reaction is performed taking the synthesized cDNA as the template. Here, the amplification reaction can be performed using an isothermal amplification reaction system that uses strand displacement polymerase, or alternatively through an ordinary PCR reaction system, for example. Thus, it is possible to inhibit the synthesis of non-specific cDNA that is not related to a target RNA, so that specific synthesis of cDNA for a desired target RNA is possible. Thus, by adopting the extreme thermophile SSB mutant protein of the invention in a reverse transcription system, it is possible to specifically and efficiently synthesize cDNA for a desired target RNA.

There are no particular restrictions regarding the RNA, possible examples include total RNA, mRNA, tRNA, and rRNA The RNA is prepared using a method known to the public from a cell or tissue expressing, or which is expected to be capable of expressing, a desired gene. For example, it is possible to use guanidine/cesium TFA method, the lithium chloride/urea method, or AGPC method, for example. There are no restrictions to the primer as long as it anneals to the template RNA in the reaction conditions that are adopted, and as mentioned above, it is possible to use a random primer, an oligo dT primer, or a target gene specific primer. Here, the target gene specific primer has a base sequence that is complementary to a specific template RNA, and preferably the 3' end of the primer that is used in an ordinary PCR reaction system is employed.

WORKING EXAMPLES

Working Example 1

Effect of the Extreme Thermophile SSB Mutant Protein on the Isothermal Amplification Reaction System—1

An experiment was conducted to evaluate the effect that the extreme thermophile SSB mutant protein has on an isothermal amplification reaction system that uses a strand-displacement polymerase by comparison with the case for the extreme thermophile SSB protein, and it was found that the extreme thermophile SSB mutant protein of the invention can improve specificity for the template nucleic acid.

Methods

An isothermal amplification reaction using a strand displacement polymerase was performed in the presence of the extreme thermophile SSB protein and the extreme thermophile SSB mutant protein, and the effects on the amplification of the template nucleic acid were compared. 20 samples of the reaction solution (10 μL) were prepared, 10 of which each included 1 ng of the template nucleic acid and 3.0 μg of the extreme thermophile SSB protein and the other 10 each included 1 ng of the template nucleic acid and 3.0 μg of the extreme thermophile SSB mutant protein.

The template nucleic acid used here was pUC19 DNA (for positive control, added to the TempliPhi DNA Amplification kit (made by GE Healthcare Amersham Biosciences)).

The *Thermus thermophilus* SSB protein having the amino acid sequence shown in Sequence Number 1 was used as the extreme thermophile SSB protein. Hereinafter, the *Thermus thermophilus* SSB protein without the mutation may be abbreviated as "Tth. SSB protein."

The mutant form having the amino acid sequence shown in Sequence Number 3 was used as the extreme thermophile SSB mutant protein. This mutant was obtained by substituting proline for phenylalanine 255 in the *Thermus thermophilus* SSB protein shown in Sequence Number 1 and serving as the target for comparison. This mutant may also be abbreviated as "Tth. SSB protein F255P."

The samples were subjected to amplification for 0, 0.5, 1.0, 1.5, 2.0, 2.5, 3.0, 3.5, 4.0, and 4.5 hours, respectively. The isothermal amplification reaction was performed according to the RCA method using phi29 DNA polymerase as the strand displacement polymerase and a random hexamer as the random primer. More specifically, the amplification reaction was conducted using the TempliPhi DNA Amplification kit (made by GE Healthcare Amersham Biosciences) according to manufacturer instructions.

After amplification, 2 μL was separated from each amplification reaction solution and subjected to electrophoresis in a 1.2% agarose gel, The gel after electrophoresis was stained with ethidium bromide to visualize the bands of nucleic acid.

Samples in which the experiment was performed as described above without adding any recombination-relation proteins, including the SSB protein, were produced as controls.

Results

The results are shown in FIG. 1.

In FIG. 1, lanes 1 to 10 are the controls. These show the result of performing the amplification reaction for 0, 0.5, 1.0, 1.5, 2.0, 2.5, 3.0, 9.5, 4.0, and 4.5 hours, respectively.

In FIG. 1, lanes 11 to 20 are the samples in which the amplification reaction was performed in the presence of the Tth. SSB protein. These show the result after performing the amplification reaction for 0, 0.5, 1.0, 1.5, 2.0, 2.5, 3.0, 3.5, 4.0, and 4.5 hours, respectively.

In FIG. 1, lanes 21 to 80 are the samples in which the amplification reaction was performed in the presence of the Tth. SSB protein F225P. These show the result after performing the amplification reaction for 0, 0.5, 1.0, 1.5, 2.0, 2.5, 3.0, 3.5, 4.0, and 4.5 hours, respectively.

When amplification was performed after adding the Tth. SSB protein F255P, it was confirmed that DNA fragments specific to the pUC19 DNA, which is the template nucleic acid, could be amplified (FIG. 1, lanes 21 to 80). On the other hand, the amplification product that was observed when amplification was performed after adding the Tth. SSB protein is very likely background noise that is not related to the template nucleic acid (FIG. 1, lanes 11 to 20). To further verify the above results, a further test was performed in Working Example 2.

Working Example 2

Effect of the Extreme Thermophile SSB Mutant Protein on the Isothermal Amplification Reaction System—2

An experiment was conducted to evaluate the effect that the extreme thermophile SSB mutant protein has on non-specific amplification an isothermal amplification reaction system by comparison with the case of the extreme thermophile SSB protein.

Methods

The isothermal amplification reaction was performed in the presence of the extreme thermophile SSB protein (Tth. SSB protein) and the extreme thermophile SSB mutant protein (Tth. SSB protein F255P), and the respective effects that these have on non specific amplification were compared. Except for the fact that pUC19 DNA was not added as a template, the experiment was conducted in the same manner as in Working Example 1.

Results

Figure 2:
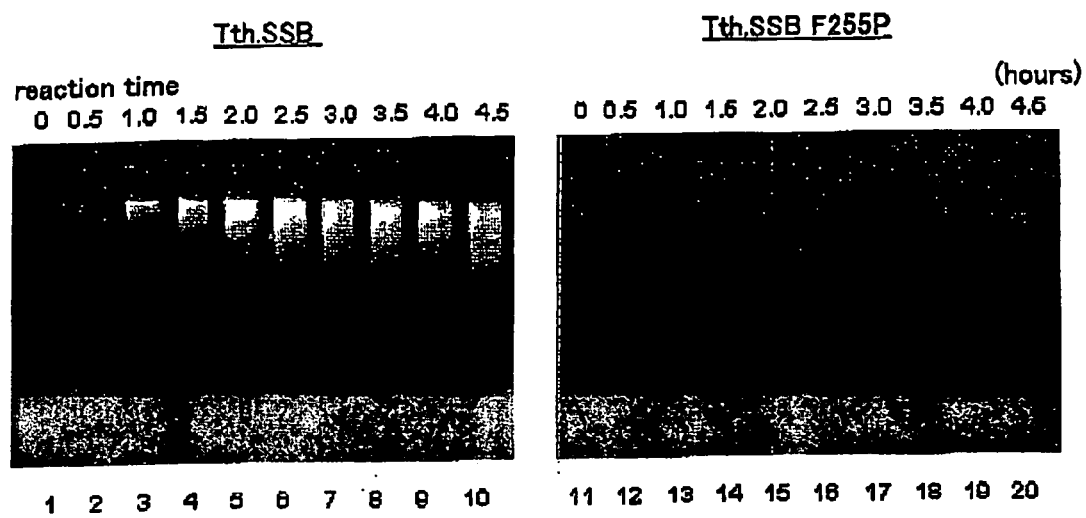
FIG. 2 is an electrophoresis pattern showing the results of Working Example 2, in which the effects that the extreme thermophile SSB protein and the extreme thermophile SSB mutant protein have on the isothermal amplification reaction system when the template nucleic acid is not present are compared and evaluated.
Figure 3:
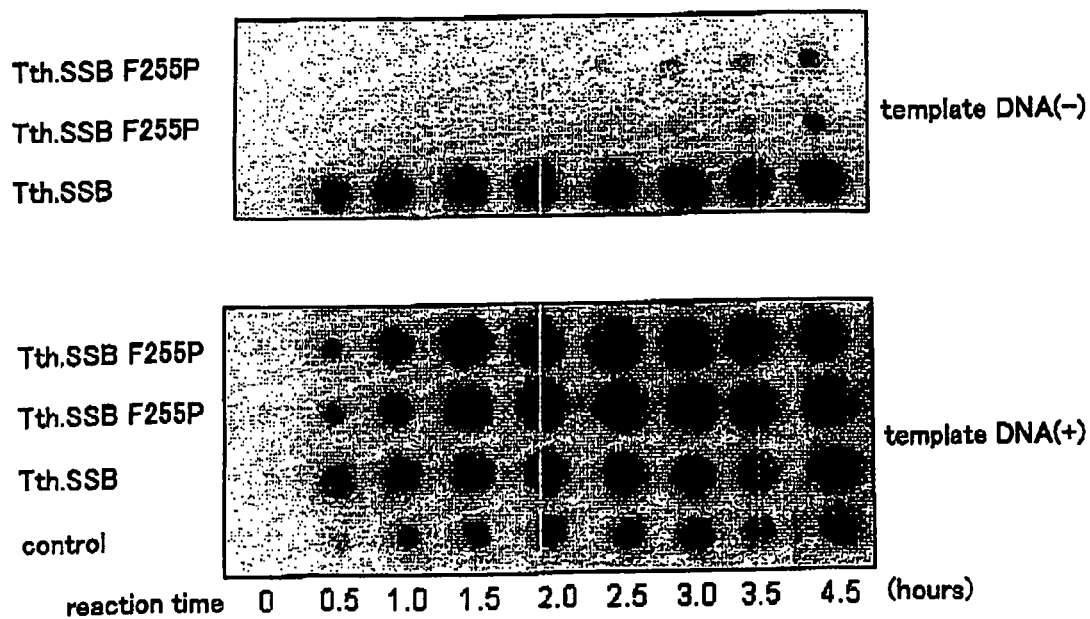
FIG. 3 is a blot showing the results of Working Example 8, in which the effects that the extreme thermophile SSB protein and the extreme thermophile SSB mutant protein have on the isothermal amplification reaction system are examined by hybridization.

The results are shown in FIG. 2.

In FIG. 2, lanes 1 to 10 are the samples in which the isothermal amplification reaction was performed in the presence of the Tth. SSB protein. These show the result after performing the amplification reaction for 0, 0.5, 1.0, 1.5, 2.0, 2.5, 3.0, 3.6, 4.0, and 4.5 hours, respectively.

In FIG. 2, lanes 11 to 20 are the samples in which the isothermal amplification reaction was performed in the presence of the Tth. SSB protein F255P. These show the result after performing the amplification reaction for 0, 0.5, 1.0, 1.6, 2.0, 2.5, 3.0, 3.5, 4.0, and 4.6 hours, respectively.

When amplification was performed after adding the Tth. SSB protein F255P, an amplification product was not observed (FIG. 2, lanes 11 to 20). On the other hand, when amplification was performed after adding the Tth. SSB protein, an amplification product was observed even though a template nucleic acid had not been added (FIG. 2, lanes 1 to 10). The amplification product observed here is not related to the template nucleic acid, and conceivably is background noise due to the formation of primer dimers, for example. Thus, adding the Tth. SSB protein F255P allows non specific amplification to be inhibited, whereas with the Tth. SSB protein it was confirmed that non-specific amplification cannot be inhibited.

Looking at these results in tandem with the results of the Working Example 1, when the Tth. SSB protein F255P was added the fact that an amplification product was obtained only in the presence of the template nucleic acid (compare FIG. 1 lanes 21 to 30 and FIG. 2 lanes 11 to 20) leads to the conclusion that the Tth. SSB protein F255P contributes to the specific amplification of the template nucleic acid. With the Tth. SSB protein, however, the amplification patterns obtained in the presence of the template nucleic acid in Working Example 1 (FIG. 1, lanes 11 to 20) and the amplification patterns obtained in Working Example 2 without the template nucleic acid being present (FIG. 2, lanes 1 to 10) are substantially identical. That is, the amplification product obtained in Working Example 1 was found to include many that were caused as the result of non-specific amplification unrelated to the template nucleic acid.

From the above results it was clear that adding the extreme thermophile SSB mutant protein resulted in inhibition of non-specific amplification unrelated to the template nucleic acid, allowed specific amplification of the template nucleic acid to be carried out efficiently, and can contribute to increasing the amplification efficiency. However, it was clear that adding the extreme thermophile SSB protein without the mutation does not allow non-specific amplification to be inhibited and therefore is not suited for performing amplification specific to the template nucleic acid.

Working Example 3

Effect of the Extreme Thermophile SSB Mutant Protein on the Isothermal Amplification Reaction System—3

1.5 µL was separated from each of the amplification reaction solutions of Working Example 1 and Working Example 2, spotted on a nylon membrane filter and then fixed on the filter. After fixing, these were hybridized with $^{32}$P-labeled pUC19 template nucleic acid serving as a probe, and then the spots were made visible and the amount of amplification product was confirmed. The results are shown in FIG. 8.

The amount of amplification product was compared, and it was verified that the Tth. SSB protein F255P produced substantially no amplification product when the template nucleic acid was not present and yielded the amplification product only in the presence of the template nucleic acid. With the Tth. SSB protein, however, substantially the same amount of amplification product was obtained both when the template nucleic acid was present and when it was not present. That is to sag, the amplification product that is obtained when the amplification reaction is performed after adding the Tth. SSB protein likely is non-specific amplification product that is unrelated to the template nucleic acid. Therefore, it was understood that there is a high probability that most of the amplification product that is observed when the template nucleic acid is present is background noise.

These results suggest that the extreme thermophile SSB protein without the mutation inhibits specific amplification of the template nucleic acid. Consequently, it was understood that the increase in the efficiency with which the template nucleic acid is amplified that is observed when the extreme thermophile SSB mutant protein is added is a result that is unique to the extreme thermophile SSB mutant protein.

Working Example 4

Effect of the SSB Protein Storage Buffer Solution on the Isothermal Amplification Reaction System An experiment was performed to evaluate whether or not the SSB protein storage buffer solution used to store the SSB protein has an effect on the isothermal amplification reaction system.

In Working Examples 1 to 3 it was observed that adding the extreme thermophile SSB mutant protein to the isothermal amplification system leads to the efficient production of specific amplification products. This working example assesses whether or not that effect is due to the SSB protein storage buffer solution component that is used to store the SSB protein. As the reaction solution (10 µL), 14 samples in which 0.5 µL of the SSB protein storage buffer solution were added and 14 samples in which the SSB protein storage buffer solution (0.5 µL) and the 0.3 µg of extreme thermophile SSB mutant protein were added were prepared.

The SSB protein storage buffer solution that was used was set to 1.5 M KCl, 50 mM Tris-HCl (pH 7.5), 1.0 mM EDTA, 0.5 mM DTT, 50% glycerol. The same template nucleic acid and extreme thermophile SSB mutant protein (Tth. SSB protein F255P) as in Working Examples 1 and 2 were used, and the amplification reaction was performed in the same manner as in Working Examples 1 and 2. It should be noted that the amplification reaction was performed for 0, 1.0, 1.5, 2.0, 2.5, 3.0, 3.5, 4.0, 4.5, 5.0, 5.5, 6.0, 6.5, and 7.0 hours, respectively, for the samples.

Samples in which the experiment was performed as described above without adding any other recombination-relation proteins, including the SSB protein, were produced as controls.

Results

Figure 4:
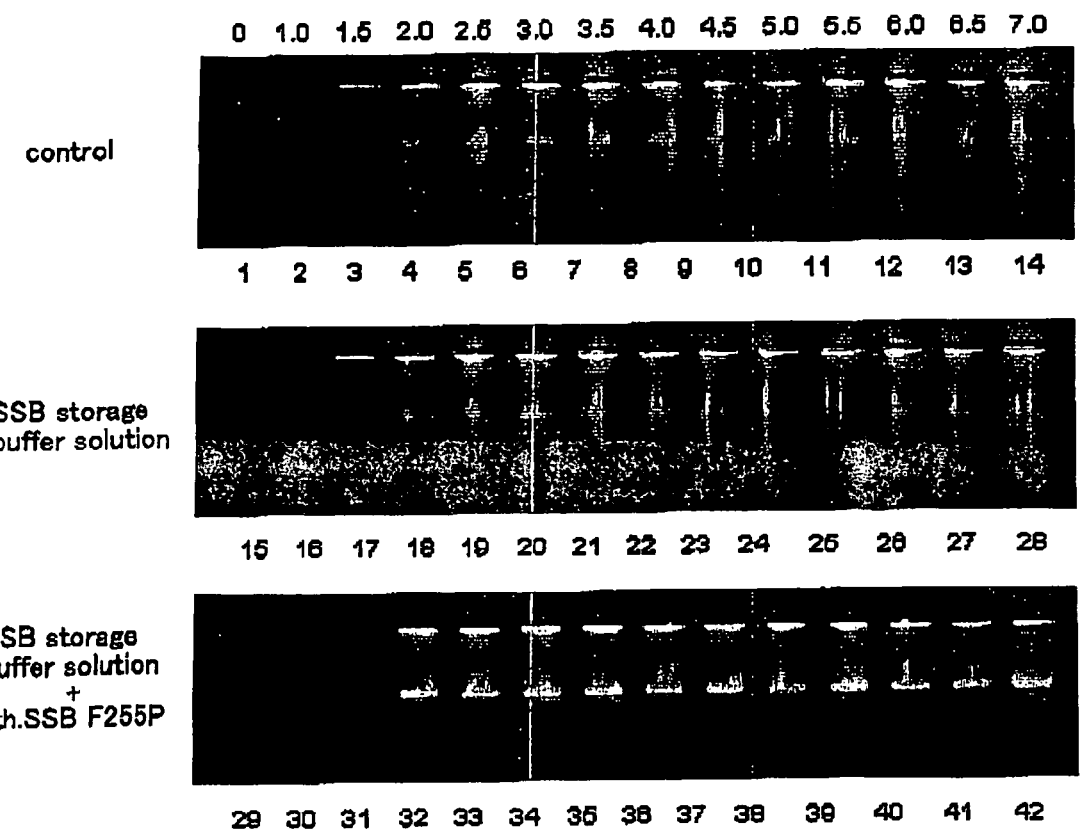
FIG. 4 is an electrophoresis pattern showing the results of Working Example 4, in which the effect that the SSB protein storage buffer solution has on the isothermal amplification reaction system was evaluated.

The results are shown in FIG. 4.

In FIG. 4, lanes 1 to 14 are the controls. These show the result of performing the amplification reaction for 0, 1.0, 1.5, 2.0, 2.5, 3.0, 3.5, 4.0, 4.5, 5.0, 5.5, 6.0, 6.5, and 7.0 hours, respectively.

In FIG. 4, lanes 15 to 28 are the samples in which the isothermal amplification reaction was performed in the presence of the SSB protein storage buffer solution. These show the result after performing the amplification reaction for 0, 1.0, 1.5, 2.0, 2.5, 3.0, 3.5, 4.0, 4.5, 5.0, 5.5, 6.0, 6.5, and 7.0 hours, respectively.

In FIG. 4, lanes 29 to 42 are the samples in which the isothermal amplification reaction was performed in the presence of the Tth. SSB protein F255P and the SSB protein storage buffer solution. These show the result after performing the amplification reaction for 0, 1.0, 1.5, 2.0, 2.5, 3.0, 3.5, 4.0, 4.5, 5.0, 5.5, 6.0, 6.5, and 7.0 hours, respectively.

Figure 5:
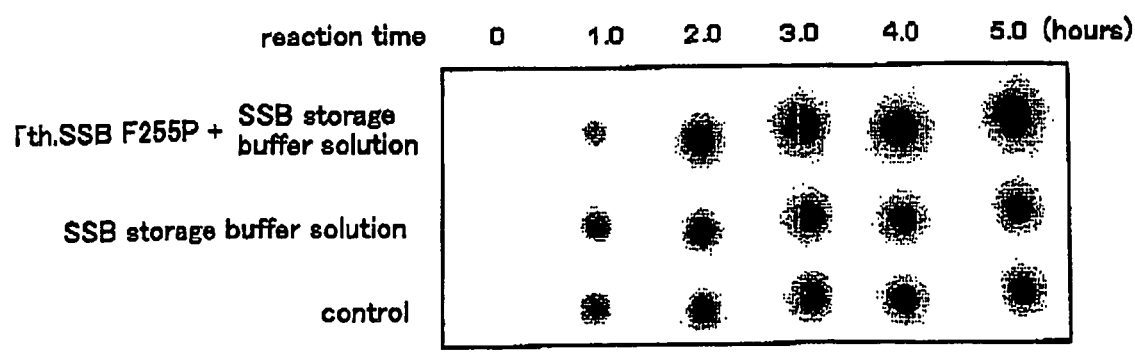
FIG. 5 is a blot showing the results of Working Example 4, in which the effect that the SSB protein storage buffer solution has on the isothermal amplification reaction system was evaluated by hybridization.

Of the amplification reaction solutions of Working Example 3, 1.5 µL was separated from each of the reaction solutions after 0, 1.0, 2.0, 3.0, 4.0, and 5.0 hours amplification, spotted on a nylon membrane filter and then fixed on the filter. Upon fixing, these were hybridized with $^{32}$P-labeled pUC19 template nucleic acid serving as the probe, and then the spots were made visible and the amount of amplification product was confirmed. The results are shown in FIG. 5.

The amount of amplification product when the storage buffer solution was added was not significantly different from the control (compare lanes 1 to 14 and lanes 16 to 28 in FIG. 4; FIG. 5). A significant increase in the amount of amplification product was observed when the Tth. SSB protein F255P was added, compared to the control and the case with only the storage buffer solution, particularly after three or more hours of amplification, (compare lanes 29 to 42 in FIG. 4 with the other lanes; FIG. 5).

From the above results it can be understood that the production of specific amplification products due to the addition of the extreme thermophile SSB mutant protein that was observed in Working Examples 1 to 3 was not affected by the SSB protein storage buffer solution, and rather this action is due to the extreme thermophile SSB mutant protein.

Working Example 5

Effects of Various Recombination-Related Proteins on the Isothermal Amplification Reaction System—1

In Working Examples 1 to 3, it was confirmed that the extreme thermophile SSB mutant protein increases the specificity of the strand displacement polymerase for the template nucleic acid in the isothermal amplification reaction. In Working Examples 5 to 7 discussed below, experiments were performed to compare and evaluate whether various other recombination-related proteins have an effect on the isothermal amplification reaction system.

Methods

To the isothermal amplification reaction system were added one of the various recombination-related proteins that are known as strand displacement factors or replication assisting proteins to confirm the manner in which DNA fragments from the target DNA are amplified and the manner in which background noise is generated. The recombination-related proteins used in the experiment are detailed below.

*Thermus thermophilus* HB8 RecO Protein (hereinafter, may be abbreviated as "Tth. RecO Protein")

*E. coli* RecA Protein (hereinafter, may be abbreviated as "*E. coli* RecA Protein")

*Thermus thermophilus* HB8 RecA Protein (hereinafter, may be abbreviated as "Tth. RecA Protein")

*E. coli* SSB Protein (hereinafter, may be abbreviated as "*E. coli* SSB Protein")

*Thermus thermophilus* HB8 SSB mutant protein (this mutant form is the Tth. SSB protein F255P used in Working Examples 1 to 4)

T4 gene 32 protein

Samples including a reaction solution (10 µL), template nucleic acid (1 ng), and 3.0 µg of one of the above recombination proteins were prepared, one for each of the recombination proteins. Further, for each of the recombination proteins, a sample was prepared in the same way except that the template nucleic acid was not added. The template nucleic acid and the isothermal amplification reaction are identical to those of Working Examples 1 to 8. After performing the amplification reaction for 24 hours, the amplification reaction was stopped by heat denaturing the proteins at 65° C. for 10 minutes. 5 µL of each reaction solution after the amplification reaction was fractioned off and subjected to 1% agarose electrophoresis. Electrophoresis was performed according to a standard method for 45 minutes at 4.5 V/cm. After electrophoresis, ethidium bromide staining was performed to visualize the amplification product.

Controls were produced without adding any of the recombination-relation proteins, and the same experiment was above was performed.

Results

Figure 6:
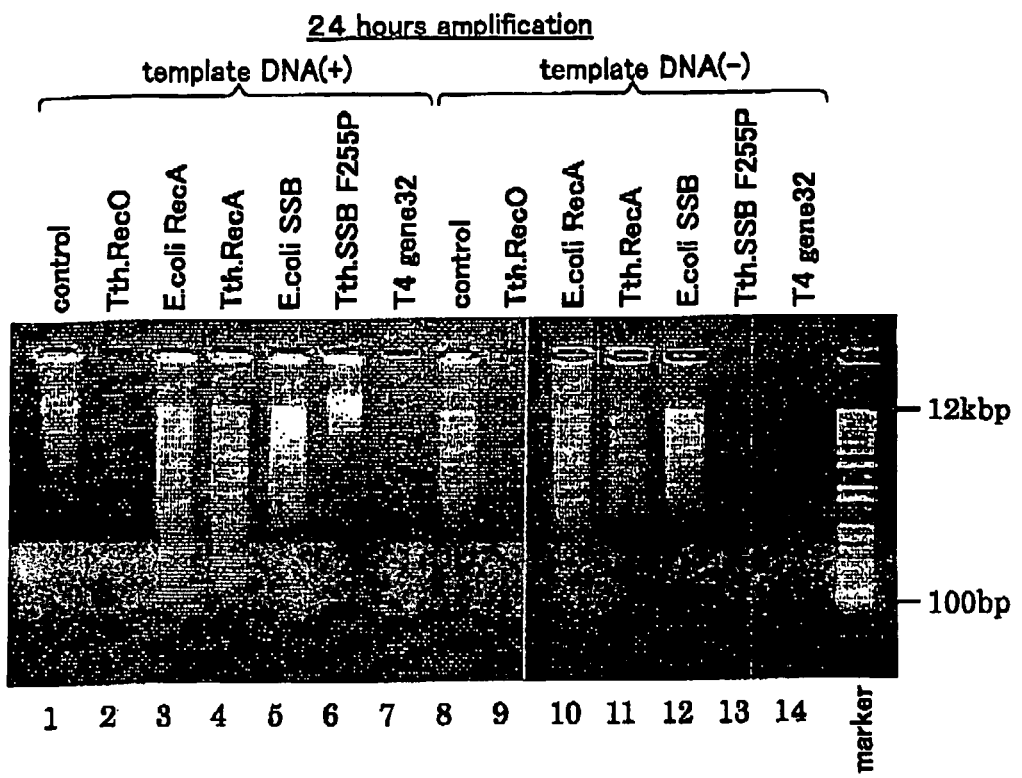
FIG. 6 is an electrophoresis pattern showing the results of Working Example 6, in which an isothermal amplification reaction was performed for 24 hours after adding any one of various types of proteins that are recognized as strand displacement factors, and then the state of amplification of the target DNA fragment and the state of background noise that is generated was confirmed.

The results are shown in FIG. 6.

In FIG. 6, lanes 1 to 7 show the results of the amplification reaction performed in the presence of the template nucleic acid.

Lane 1 is the control.

Lane 2 shows the results when the Tth. RecO Protein was added;

Lane 3 shows the results when the *E. coli* RecA Protein was added;

Lane 4 shows the results when the Tth. RecA Protein was added;

Lane 5 shows the results when the *E. coli* SSB Protein was added;

Lane 6 shows the results when the Tth. SSB protein P255P was added; and

Lane 7 shows the results when the T4 gene 32 protein was added.

In FIG. 6, lanes 8 to 14 show the results of the amplification reaction performed when template nucleic acid is not present.

Lane 8 is the control.

Lane 9 shows the results when the Tth. RecO Protein was added;

Lane 10 shows the results when the *E. coli* RecA Protein was added;

Lane 11 shows the results when the Tth. RecA Protein was added;

Lane 12 shows the results when the *E. coli* SSB Protein was added;

Lane 13 shows the results when the Tth. SSB protein F255P was added; and

Lane 14 shows the results when the T4 gene 32 protein was added.

It was found that when the amplification reaction is performed after adding the Tth. SSB protein F255P (FIG. 6, lane 6), it is possible to amplify DNA fragments that are specific for the target pUC19 DNA. That no amplification product was observed when the template nucleic acid is not present (FIG. 6, lane 18) demonstrates that specific amplification of the template nucleic acid is due to the addition of the Tth. SSB protein F255P.

On the other hand, in the control, an amplification product from the pUC19 DNA was confirmed (FIG. 6, lane 1), but an amplification product also was observed when the amplification reaction was performed without adding the template nucleic acid (FIG. 6, lane 8). This is the result of non-specific amplification that is unrelated to the template nucleic acid that is caused by the formation of a primer dimer, for example, and the same non-specific amplification also was observed when the *E. coli* RecA Protein, the Tth. RecA Protein, and the *E. coli* SSB Protein were added (FIG. 6, lanes 10 to 12). The amplification pattern when the template was not present that was observed with the *E. coli* RecA Protein, the Tth. RecA Protein, and the *E. coli* SSB Protein resembles the amplification pattern that was obtained when amplification was performed in the presence of these proteins after adding the template nucleic acid. This suggests that the amplification product that was obtained when the template nucleic acid had been added is not an amplification product that is related to the template nucleic acid but rather is an amplification product that is obtained as the result of non-specific amplification. On the other hand, it is conceivable that amplification of the template nucleic acid is being suppressed. When the Tth. RecO protein and the T4 gene 32 protein were added, amplification was hindered and amplification product could not be obtained both when the template nucleic acid was present and when it was not present (FIG. 6, lanes 2 and 9, and lanes 7 and 14).

The above results show that adding the extreme thermophile SSB mutant protein allows non-specific amplification that is unrelated to the template nucleic acid to be suppressed. From this finding it was evident that adding the extreme thermophile SSB mutant protein to the isothermal amplification system allows amplification that is specific to the template nucleic acid to be performed efficiently and with high precision. When the amplification reaction is performed after adding recombination-related proteins other than the extreme thermophile SSB mutant protein of the invention, not only is it not possible to inhibit non-specific amplification, but it is also believed that amplification of the template nucleic acid is hindered. However, when the amplification reaction is performed upon adding the extreme thermophile SSB mutant protein, it is thought that such impediments to amplification can be inhibited. When the T4 gene 32 protein and the Tth. RecO Protein were added, it was found that, although non-specific amplification could be inhibited, amplification of the template nucleic acid also was hindered. That is, it was clear that use of the T4 gene 32 protein and the Tth. RecO Protein is disadvantageous because it is necessary to appropriately control the amount added to the reaction system, for example, and the procedure for this is complicated.

Working Example 6

Effects of Various Recombination-Related Proteins on the Isothermal Amplification Reaction System—2

In continuation of Working Example 5, an experiment was performed to compare and evaluate the effects that the various recombination-related proteins have on the isothermal amplification reaction system.

Methods

The effects that the various recombination-related proteins have on the isothermal amplification reaction system were assessed in the same manner as in Working Example 5, except that the amplification time was set to 18 hours.

Results

Figure 7:
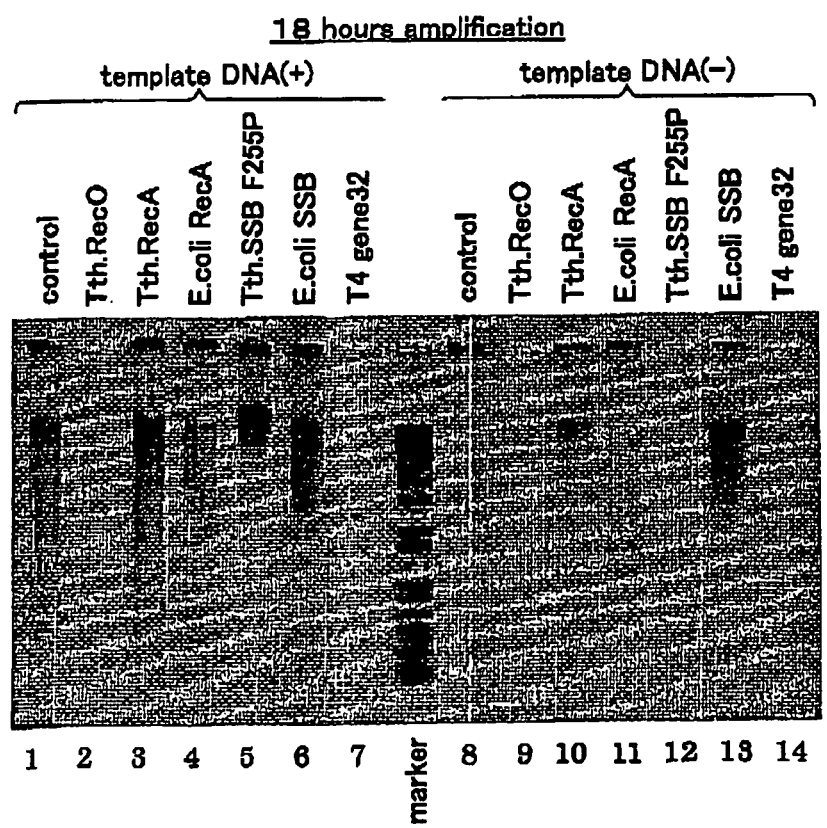
FIG. 7 is an electrophoresis pattern showing the results of Working Example 6, in which an isothermal amplification reaction was performed for 18 hours after adding any one of various types of proteins that are recognized as strand displacement factors, and then the state of amplification of the target DNA fragment and the state of background noise that is generated was confirmed.

The results are shown in FIG. 7.

In FIG. 7, lanes 1 to 7 show the results of the amplification reaction performed in the presence of the template nucleic acid.

Lane 1 is the control.

Lane 2 shows the results when the Tth. RecO Protein was added;

Lane 3 shows the results when the Tth. RecA Protein was added;

Lane 4 shows the results when the E. coli RecA Protein was added;

Lane 5 shows the results when the Tth. SSB Protein F255P was added;

Lane 6 shows the results when the E. coli SSB protein was added; and

Lane 7 shows the results when the T4 gene 32 protein was added.

In FIG. 7, lanes 8 to 14 show the results of the amplification reaction performed when the template nucleic acid is not present.

Lane 8 is the control.

Lane 9 shows the results when the Tth. RecO Protein was added;

Lane 10 shows the results when the Tth. RecA Protein was added;

Lane 11 shows the results when the E. coli RecA Protein was added;

Lane 12 shows the results when the Tth. SSB Protein F255P was added;

Lane 13 shows the results when the E. coli SSB protein was added; and

Lane 14 shows the results when the T4 gene 32 protein was added.

Like in Working Example 5, it was clear that that when the amplification reaction is performed after adding the Tth. SSB protein F255P, it is possible to amplify DNA fragments specific for the pUC19 DNA, which is the template nucleic acid (FIG. 7, compare lane 5 and lane 12).

On the other hand, when Tth. RecA Protein, E. coli RecA Protein, and E. coli SSB Protein were added when the template nucleic acid is present (FIG. 7, lanes 3, 4, and 6), an amplification product of the same size as that of the amplification product obtained by performing the amplification reaction without adding the template nucleic acid (FIG. 7, lanes 10, 11, and 13) was confirmed. The amplification product that was obtained by amplification when the template nucleic acid is not present is likely background noise that is due to a primer dimer, for example, and is not a DNA fragment that is specific to the template nucleic acid. Thus it was clear that the addition of these proteins does not allow the effect of inhibiting non-specific amplification to be achieved.

When the above results are considered in conjunction with the results of Working Example 5, the fact that the same results are obtained even though the reaction time was changed clearly indicates that a change in the reaction time does not result in a change in the action of the extreme thermophile SSB mutant protein.

Working Example 7

Effects of Various Recombination-Related Proteins on the Isothermal Amplification Reaction System (Restriction Enzyme Processing)—3

5 µL was fractioned off of each reaction solution after the isothermal amplification that was used in Working Example 6 and processed with restriction enzymes. As for the restriction enzyme processing, 10 units of the restriction enzyme EcoRI were used and the reaction was carried out for 2 hours at 37° C.

After the processing with the restriction enzyme, the product was subjected to electrophoresis in 1% agarose gel, The electrophoresis was performed using the same method as in Working Examples 6 and 6.

The results are shown in FIG. 8.

Lanes 1 to 14 in FIG. 8 correspond to lanes 1 to 14 in FIG. 7.

In the control and in the presence of Tth. RecA Protein, E. coli RecA Protein, Tth. SSB Protein F255P, and E. coli SSB Protein, it was confirmed that DNA fragments specific to pUC19 DNA, which is the template nucleic acid, were included (FIG. 8, lanes 1 and 8 to 6).

With the Tth. RecA Protein, however, an amplification product band also was confirmed when the amplification reaction was performed without adding the template nucleic acid (FIG. 8, lane 10). This means that DNA fragments that are non-specific for the template nucleic acid are included in the amplification product produced by the amplification reaction. Even when the template nucleic acid had been added, the presence of DNA molecules that were not cleaved by the restriction enzyme EcoRI was confirmed on the electrophoresis gel. This suggests that these are DNA fragments that are caused by amplification that is non-specific for the template nucleic acid.

It should be noted that non-specific amplification product was similarly detected in the case of the E. coli RecA Protein and the E. coli SSB Protein as well (in FIG. 8, compare lanes 4 and 11, and lanes 6 and 13).

From these results it is clear that only in the sample to which the extreme thermophile SSB mutant protein had been added was it possible to inhibit the amplification of DNA fragments that are non-specific to pUC19 DNA, which is the template nucleic acid. On the other hand, it is clear that this effect cannot be obtained when the other recombination proteins are present.

The invention claimed is:

1. A single-stranded DNA binding protein comprising the amino acid sequence of SEQ ID NO: 3, wherein:
the protein is capable of increasing amplification efficiency of a template nucleic acid in an isothermal amplification reaction system that uses a strand displacement polymerase.

2. The protein according to claim 1, wherein the protein exhibits an interaction with the strand displacement polymerase different from a protein having the amino acid sequence of SEQ ID NO: 1.

3. The protein according to claim 1, wherein the protein exhibits a DNA binding ability different from a protein having the amino acid sequence of SEQ ID NO: 1.

4. A single-stranded DNA binding protein consisting of the amino acid sequence of SEQ ID NO: 3.

* * * * *

SEQUENCE LISTING

<160> NUMBER OF SEQ ID NOS: 6

<210> SEQ ID NO 1
<211> LENGTH: 263
<212> TYPE: PRT
<213> ORGANISM: Thermus thermophilus

<400> SEQUENCE: 1

```
Met Ala Arg Gly Leu Asn Arg Val Phe Leu Ile Gly Ala Leu Ala Thr
1               5                   10                  15

Arg Pro Asp Met Arg Tyr Thr Pro Ala Gly Leu Ala Ile Leu Asp Leu
            20                  25                  30

Thr Leu Ala Gly Gln Asp Leu Leu Ser Asp Asn Gly Gly Glu Arg
        35                  40                  45

Glu Val Ser Trp Tyr His Arg Val Arg Leu Leu Gly Arg Gln Ala Glu
    50                  55                  60

Met Trp Gly Asp Leu Leu Asp Gln Gly Gln Leu Val Phe Val Glu Gly
65                  70                  75                  80

Arg Leu Glu Tyr Arg Gln Trp Glu Arg Glu Gly Glu Lys Arg Ser Glu
                85                  90                  95

Leu Gln Ile Arg Ala Asp Phe Leu Asp Pro Leu Asp Asp Arg Gly Lys
            100                 105                 110

Glu Arg Ala Glu Asp Ser Arg Gly Gln Pro Arg Leu Arg Ala Ala Leu
        115                 120                 125

Asn Gln Val Phe Leu Met Gly Asn Leu Thr Arg Asp Pro Glu Leu Arg
    130                 135                 140

Tyr Thr Pro Gln Gly Thr Ala Val Ala Arg Leu Gly Leu Ala Val Asn
145                 150                 155                 160

Glu Arg Arg Gln Gly Ala Glu Glu Arg Thr His Phe Val Glu Val Gln
                165                 170                 175

Ala Trp Arg Asp Leu Ala Glu Trp Ala Ala Glu Leu Arg Lys Gly Asp
            180                 185                 190

Gly Leu Phe Val Ile Gly Arg Leu Val Asn Asp Ser Trp Thr Ser Ser
        195                 200                 205

Ser Gly Glu Arg Arg Phe Gln Thr Arg Val Glu Ala Leu Arg Leu Glu
    210                 215                 220

Arg Pro Thr Arg Gly Pro Ala Gln Ala Gly Gly Ser Arg Ser Arg Glu
225                 230                 235                 240

Ala Gln Thr Gly Gly Val Asp Ile Asp Glu Gly Leu Glu Asp Phe Pro
                245                 250                 255

Pro Glu Glu Asp Leu Pro Phe
            260
```

<210> SEQ ID NO 2
<211> LENGTH: 792
<212> TYPE: DNA
<213> ORGANISM: Thermus thermophilus

<400> SEQUENCE: 2

```
atggctcgag gcctgaaccg cgttttccta atcggcgccc tcgccacccg gccggacatg      60
cgctacactc cggcgggggct cgccattttg gacctgaccc tcgccggtca ggacctgctc     120
ctttccgata acggggggga gcgggaggtg tcctggtacc accgggtgag gctcttaggc    180
cgccaggcgg agatgtgggg cgacctcttg gaccaagggc agctcgtctt cgtggagggc    240
cgcctggagt accgccagtg ggaaagggag ggggagaagc ggagcgagct ccagatccgg    300
```

```
gccgacttcc tggaccccct ggacgaccgg gggaaggagc gggcggagga cagccggggc    360
cagcccaggc tccgcgccgc cctgaaccag gtcttcctca tgggcaacct gacccgggac    420
ccggaactcc gctacacccc ccagggcacc gcggtggccc ggctgggcct ggcggtgaac    480
gagcgccgcc agggggcgga ggagcgcacc cacttcgtgg aggttcaggc ctggcgcgac    540
ctggcggagt gggccgccga gctgaggaag ggcgacggcc ttttcgtgat cggcaggttg    600
gtgaacgact cctggaccag ctccagcggc gagcggcgct ttcagacccg tgtggaggcc    660
ctcaggctgg agcgcccac ccgtggacct gcccaggccg gcggaagcag gtcccgcgaa    720
gcccagacgg gtggggtgga cattgacgaa ggcttggaag actttccgcc ggaggaggat    780
ttgccgtttt ga                                                       792
```

```
<210> SEQ ID NO 3
<211> LENGTH: 263
<212> TYPE: PRT
<213> ORGANISM: Artificial Sequence
<220> FEATURE:
<223> OTHER INFORMATION: Synthetic Peptide

<400> SEQUENCE: 3

Met Ala Arg Gly Leu Asn Arg Val Phe Leu Ile Gly Ala Leu Ala Thr
1               5                   10                  15

Arg Pro Asp Met Arg Tyr Thr Pro Ala Gly Leu Ala Ile Leu Asp Leu
            20                  25                  30

Thr Leu Ala Gly Gln Asp Leu Leu Ser Asp Asn Gly Gly Glu Arg
        35                  40                  45

Glu Val Ser Trp Tyr His Arg Val Arg Leu Leu Gly Arg Gln Ala Glu
    50                  55                  60

Met Trp Gly Asp Leu Leu Asp Gln Gly Gln Leu Val Phe Val Glu Gly
65                  70                  75                  80

Arg Leu Glu Tyr Arg Gln Trp Glu Arg Gly Glu Lys Arg Ser Glu
                85                  90                  95

Leu Gln Ile Arg Ala Asp Phe Leu Asp Pro Leu Asp Asp Arg Gly Lys
            100                 105                 110

Glu Arg Ala Glu Asp Ser Arg Gly Gln Pro Arg Leu Arg Ala Ala Leu
        115                 120                 125

Asn Gln Val Phe Leu Met Gly Asn Leu Thr Arg Asp Pro Glu Leu Arg
130                 135                 140

Tyr Thr Pro Gln Gly Thr Ala Val Ala Arg Leu Gly Leu Ala Val Asn
145                 150                 155                 160

Glu Arg Arg Gln Gly Ala Glu Glu Arg Thr His Phe Val Glu Val Gln
                165                 170                 175

Ala Trp Arg Asp Leu Ala Glu Trp Ala Ala Glu Leu Arg Lys Gly Asp
            180                 185                 190

Gly Leu Phe Val Ile Gly Arg Leu Val Asn Asp Ser Trp Thr Ser Ser
        195                 200                 205

Ser Gly Glu Arg Arg Phe Gln Thr Arg Val Glu Ala Leu Arg Leu Glu
    210                 215                 220

Arg Pro Thr Arg Gly Pro Ala Gln Ala Gly Ser Arg Ser Arg Glu
225                 230                 235                 240

Ala Gln Thr Gly Gly Val Asp Ile Asp Glu Gly Leu Glu Asp Pro Pro
                245                 250                 255

Pro Glu Glu Asp Leu Pro Phe
            260
```

-continued

<210> SEQ ID NO 4
<211> LENGTH: 264
<212> TYPE: PRT
<213> ORGANISM: Thermus aquaticus

<400> SEQUENCE: 4

Met Ala Arg Gly Leu Asn Gln Val Phe Leu Ile Gly Thr Leu Thr Ala
1               5                   10                  15

Arg Pro Asp Met Arg Tyr Thr Pro Gly Gly Leu Ala Ile Leu Asp Leu
            20                  25                  30

Asn Leu Ala Gly Gln Asp Ala Phe Thr Asp Glu Ser Gly Gln Glu Arg
        35                  40                  45

Glu Val Pro Trp Tyr His Arg Val Arg Leu Leu Gly Arg Gln Ala Glu
    50                  55                  60

Met Trp Gly Asp Leu Leu Glu Lys Gly Gln Leu Ile Phe Val Glu Gly
65                  70                  75                  80

Arg Leu Glu Tyr Arg Gln Trp Gly Lys Asp Gly Glu Lys Lys Ser Glu
                85                  90                  95

Val Gln Val Arg Ala Glu Phe Ile Asp Pro Leu Glu Gly Arg Gly Arg
            100                 105                 110

Glu Thr Leu Glu Asp Ala Arg Gly Gln Pro Arg Leu Arg Arg Ala Leu
        115                 120                 125

Asn Gln Val Ile Leu Met Gly Asn Leu Thr Arg Asp Pro Asp Leu Arg
    130                 135                 140

Tyr Thr Pro Gln Gly Thr Ala Val Val Arg Leu Gly Leu Ala Val Asn
145                 150                 155                 160

Glu Arg Arg Arg Gly Gln Glu Glu Arg Thr His Phe Leu Glu Val
                165                 170                 175

Gln Ala Trp Arg Glu Leu Ala Glu Trp Ala Ser Glu Leu Arg Lys Gly
            180                 185                 190

Asp Gly Leu Leu Val Ile Gly Arg Leu Val Asn Asp Ser Trp Thr Ser
        195                 200                 205

Ser Ser Gly Glu Arg Arg Phe Gln Thr Arg Val Glu Ala Leu Arg Leu
    210                 215                 220

Glu Arg Pro Thr Arg Gly Pro Ala Gln Ala Gly Ser Arg Pro Pro
225                 230                 235                 240

Thr Val Gln Thr Gly Gly Val Asp Ile Asp Glu Gly Leu Glu Asp Phe
                245                 250                 255

Pro Pro Glu Glu Asp Leu Pro Phe
            260

<210> SEQ ID NO 5
<211> LENGTH: 795
<212> TYPE: DNA
<213> ORGANISM: Thermus aquaticus

<400> SEQUENCE: 5
atggctcgag gcctgaacca agtattcctc atcggcaccc tgaccgcccg ccccgacatg      60
cgctacaccc cgggaggcct ggccatcttg gacctgaacc tggcgggaca ggatgccttc     120
acggacgagt ccggccaaga gagggaagtc ccctggtacc accgggttag gcttctgggc     180
cgccaggcgg agatgtgggg ggaccttctg gaaaagggcc agctcatctt cgtggaaggg     240
cgcctggagt accgccagtg ggagaaggac ggggagaaga gagcgaagt gcaggtgcgg      300 gccgagttca ttgaccccct ggaggggagg ggccgggaga ccctggagga cgccgggc       360 cagcccaggc ttcgccgggc cctgaaccag gtgatcctca tgggcaacct caccgggac     420

```
cccgacctcc gctacacccc tcaggggacg gcggtggtgc gcctgggcct ggcggtcaac      480
gagcgccgcc ggggccagga agaggagagg acccacttcc tcgaggttca ggcctggcgc      540
gagctggcgg agtgggcttc ggagcttagg aagggcgacg ggcttttggt catcggccgt      600
ttggtgaacg actcctggac gagctccagc ggagagaggc gcttccagac ccgtgtggaa      660
gccctcaggc tggagcgccc cacccgtggg cctgcccaag ccggcggaag caggccccccc     720 acggtccaga cgggcggggt ggacatagac gaagggctgg aagacttccc gccggaggag      780
gatttgccgt tttga                                                       795
```

<210> SEQ ID NO 6
<211> LENGTH: 264
<212> TYPE: PRT
<213> ORGANISM: Artificial Sequence
<220> FEATURE:
<223> OTHER INFORMATION: Synthetic Peptide

<400> SEQUENCE: 6

```
Met Ala Arg Gly Leu Asn Gln Val Phe Leu Ile Gly Thr Leu Thr Ala
1               5                   10                  15

Arg Pro Asp Met Arg Tyr Thr Pro Gly Gly Leu Ala Ile Leu Asp Leu
            20                  25                  30

Asn Leu Ala Gly Gln Asp Ala Phe Thr Asp Glu Ser Gly Gln Glu Arg
        35                  40                  45

Glu Val Pro Trp Tyr His Arg Val Arg Leu Leu Gly Arg Gln Ala Glu
    50                  55                  60

Met Trp Gly Asp Leu Leu Glu Lys Gly Gln Leu Ile Phe Val Glu Gly
65                  70                  75                  80

Arg Leu Glu Tyr Arg Gln Trp Glu Lys Asp Gly Glu Lys Lys Ser Glu
                85                  90                  95

Val Gln Val Arg Ala Glu Phe Ile Asp Pro Leu Glu Gly Arg Gly Arg
            100                 105                 110

Glu Thr Leu Glu Asp Ala Arg Gly Gln Pro Arg Leu Arg Arg Ala Leu
        115                 120                 125

Asn Gln Val Ile Leu Met Gly Asn Leu Thr Arg Asp Pro Asp Leu Arg
    130                 135                 140

Tyr Thr Pro Gln Gly Thr Ala Val Val Arg Leu Gly Leu Ala Val Asn
145                 150                 155                 160

Glu Arg Arg Arg Gly Gln Glu Glu Glu Arg Thr His Phe Leu Glu Val
                165                 170                 175

Gln Ala Trp Arg Glu Leu Ala Glu Trp Ala Ser Glu Leu Arg Lys Gly
            180                 185                 190

Asp Gly Leu Leu Val Ile Gly Arg Leu Val Asn Asp Ser Trp Thr Ser
        195                 200                 205

Ser Ser Gly Glu Arg Arg Phe Gln Thr Arg Val Glu Ala Leu Arg Leu
    210                 215                 220

Glu Arg Pro Thr Arg Gly Pro Ala Gln Ala Gly Ser Arg Pro Pro
225                 230                 235                 240

Thr Val Gln Thr Gly Gly Val Asp Ile Asp Glu Gly Leu Glu Asp Pro
                245                 250                 255

Pro Pro Glu Glu Asp Leu Pro Phe
            260
```